US006193954B1

(12) United States Patent
Adjei et al.

(10) Patent No.: US 6,193,954 B1
(45) Date of Patent: *Feb. 27, 2001

(54) FORMULATIONS FOR PULMONARY DELIVERY OF DOPAMINE AGONISTS

(75) Inventors: Akwete L. Adjei, Wadsworth; Jack Zheng, Lake Bluff; Pramod K. Gupta, Gurnee; Kennan C. Marsh, Lake Forest; Vivian Wu, Libertyville; Dennis Y. Lee, Highland Park, all of IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/822,631

(22) Filed: Mar. 21, 1997

(51) Int. Cl.$^7$ .................................. A61L 9/04; A61K 9/14
(52) U.S. Cl. .................................. 424/45; 424/46
(58) Field of Search ........................... 424/45, 46

(56) References Cited

U.S. PATENT DOCUMENTS

| | | | |
|---|---|---|---|
| 5,118,494 | * | 6/1992 | Schultz et al. ................... 424/45 |
| 5,145,684 | * | 9/1992 | Liversidge et al. ................ 424/489 |
| 5,182,097 | | 1/1993 | Byron et al. ..................... 424/45 |
| 5,190,029 | | 3/1993 | Buron et al. ..................... 128/200 |
| 5,225,183 | | 7/1993 | Purewal et al. ................... 424/45 |
| 5,348,730 | * | 9/1994 | Greenleaf et al. ................. 424/45 |
| 5,492,688 | | 2/1996 | Byron et al. ..................... 424/45 |
| 5,597,832 | | 1/1997 | Michaelides et al. .............. 514/285 |
| 5,736,124 | * | 4/1998 | Akehurst et al. .................. 424/45 |

FOREIGN PATENT DOCUMENTS

| | | |
|---|---|---|
| 9111173 | 8/1991 | (WO) . |
| 9515151 | 6/1995 | (WO) . |
| 9524892 | 9/1995 | (WO) . |

OTHER PUBLICATIONS

Andersen, P; Thienopyridine Derivatives Identified as the First Selective, Full Efficacy, Dopamine D1 Receptor Agonists; Eruopean Journal of Pharmacology 137 (1987) 291–292.

Katerinopoulos, H.; Structure Activity Relationships for Dopamine Analogs: A Review; Drugs of the Future vol. 12, No. 3. 1987. Page #s ??

Brewster W.; Trans–10,11–Dihydroxy–5,6,6a,7,8,12b–Hexahydrobenzo[a]Phenanthridine: A Highly Potent Selective Dopamine D1 Full Agonist; J. Med Chem 1990, 33, 1756–1764.

* cited by examiner

Primary Examiner—Thurman K. Page
Assistant Examiner—Susan Tran
(74) Attorney, Agent, or Firm—Regina M. Anderson

(57) ABSTRACT

The present invention relates to methods and formulations for administering a dopamine agonist to the airways of a patient. The preferred dopamine agonist is selected from (5aR-trans)-4,5,6,7,11b-hexahydro-2-propylbenzo[f]thieno[2,3-c]quinoline- 9,10)-diol, diacetate (ester) hydrochloride. The delivery method relates to certain aerosol formulations and liquid formulations which are administered into the airways to provide effective delivery of the dopamine agonists to the receptor.

31 Claims, No Drawings

FORMULATIONS FOR PULMONARY DELIVERY OF DOPAMINE AGONISTS

TECHNICAL FIELD

The present invention relates to a methods and formulations for administering a dopamine agonist to the airways of a patient.

BACKGROUND OF THE INVENTION

Dopamine is an important neurotransmitter in the central nervous system (CNS), where it is involved with motor function, perception, arousal, motivation and emotion. Dopamine imbalance is believed to play a key role in a number of CNS-related disorders such as schizophrenia, Parkinson's disease, drug abuse, eating disorders and depression. Dopamine also has several important roles in the peripheral nervous system, such as in the control of blood to the kidneys and in autonomic ganglion transmission.

Dopamine agonists such as those described in U.S. Pat. No. 5,597,832 are useful therapeutic agents. However, these agents are poorly absorbed into the systemic circulation when administered orally, probably due to acid degradation and significant liver extraction. They are, however, well absorbed when administered into the airways. This is probably due to the large absorptive area, low enzymatic activity, and near-neutral pH in the lung.

There is a need to deliver dopamine agonists which may have instability problems and/or poor bioavailability when administered orally by alternative non-invasive routes.

Numerous pharmaceutical compounds are preferentially delivered by means of metered dose inhalation (MDI) devices, in which a physiologically inert propellant of high vapor pressure is used to discharge a precise amount of medication with each operation. These MDI devices, also known as aerosols or inhalers, have found widespread use among patients suffering, for example, from episodic or chronic asthma. The propellants of choice have historically been chlorofluoro-carbons, such Propellant 11 (trichlorofluoromethane), Propellant 12 (dichlorodifluoromethane) and Propellant 114 (dichlorotetrafluoroethane).

In recent years, however, there have been growing concerns that chlorofluorocarbon (CFC) propellants have detrimental environmental effects, and in particular that they interfere with the protective upper-atmosphere ozone layer. Under an international accord (the Montreal Protocol), the use of CFC propellants will be prohibited by the start of the year 2000, and possibly sooner. Alternative propellant vehicles are being developed which exhibit little or no ozone depletion potential (ODP). Such alternative propellants include two—HFC-134a (1,1,1,2-tetrafluoroethane) and HFC-227ea (1,1,1,2,3,3,3-heptafluoropropane) which have negligible ODP and are currently undergoing safety and environmental testing.

However, halogenated alkane propellants such as HFC-134a and HFC-227ea are substantially less polar than traditional CFC propellants and many surfactants which are generally used in known MDI formulations have been found to be immiscible with or insoluble in, and therefore incompatible with, these new, non-CFC propellants. Such surfactants are necessary to prevent aggregation (in the form of "caking" or crystallization, for example) of the medicinally active compound in the reservoir of the inhaler, to facilitate uniform dosing upon aerosol administration, and to provide an aerosol spray discharge having a favorable respirable fraction (that is, a particle size distribution such that a large portion of the discharge reaches the alveoli where absorption takes place, and thus produces high lung deposition efficiencies).

U.S. Pat. No. 5,225,183 discloses a formulation comprising HFC-134a, a surface active agent, and an adjuvant or co-solvent having a higher polarity than HFC-134a Representative adjuvants or co-solvents having a higher polarity than HFC-134a include alcohols such as ethanol, isopropanol and propylene glycol; hydrocarbons such as propane, butane, isobutane, pentane, isopentane and neopentane; and other propellants such as Propellants 11, 12, 114, 113 and 142b. The adjuvant is claimed to provide a propellant system having comparable properties to those based on CFC propellants and therefore allow the use of traditional surfactants. Blends of HFC-134a with other solvents or propellants including dimethyl ether; fluorocarbons such as perfluoropropane, perfluorobutane and perfluoropentane; and hydrochlorofluorocarbons such as HCFC-123 are disclosed in U.S. Pat. No. 5,190,029.

Another approach to solving the incompatibility of HFC-134a with many surfactants is to substitute other surface active agents for those traditionally used in CFC aerosols. The use of polar surfactants such as polyethylene glycol, diethylene glycol monoethyl ether, polyoxyethylene (20) sorbitan monooleate, propoxylated polyethylene glycol, and polyoxyethylene (4) lauryl ether is disclosed in U.S. Pat. No. 5,492,688. U.S. Pat. No. 5,182,097 discloses that HFC-134a can be used as the sole propellant if oleic acid is used as the surfactant. U.S. Pat. No. 5,182,097 discloses that using fluorinated surfactants allows the HFC-134a as the sole propellant. PCT Application No. WO 91/11173 discloses that mixtures of fluorinated surfactants with conventional surfactants or other adjuvants such as polxamers or polyethylene glycols allow the use of hydrofluorocarbon propellants. Non conventional excipients which have been used to prepare aerosol formulations with halogenated alkane propellants include protective colloids, see PCT Application No. WO 95/15151, and tocopherol, see PCT Application No. WO 95/24892.

Such adjuvants, cosolvents and non-traditional surfactants or excipients may of course be physiologically active, and in some instances may not be tolerated by the user of an MDI medication. Solvent mixtures can present the manufacturer with production complexities, and the use of non-traditional ingredients results in regulatory compliance difficulties. There is, therefore, a continuing need for MDI formulations compatible with non-CFC, non-ozone depleting propellants, which prevent aggregation of drug particles without the use of cosolvents or similar carrier additives, and which provide uniformity of dosing and a favorable respirable fraction.

In addition to delivery via metered dose inhalers, other pulmonary delivery systems include powders, microparticles and aqueous and non-aqueous based solutions or dispersions which are administered through and/or into the airways by nasal or trachael routes.

SUMMARY OF THE INVENTION

Dopamine agonists such as those described below are effectively absorbed from the airways. After absorption from the lung, the drug bypasses the liver and is distributed to the body. The efficacy of fomulations administered to the lungs is similar to that obtained by injection.

Accordingly, the present invention provides a method of administering a dopamine agonist to a patient comprising administering a therapeutically effective amount of a dopamine agonist to the airways of the patient. This deliver means can occur through nasal or tracheal administration and can be in the form of a formulation or composition comprising a dopamine agonist delivered in the form of a solid, microparticle or powder and may further comprise a pulmonary delivery excipient selected from solids or liquids which are aqueous based or non-aqueous based. Liquid formulations delivered through the airways according to this invention may be prepared in aqueous or non-aqueous vehicles and delivered to the airways by means of drops or sprays. The present invention therefore relates to a composition for pulmonary delivery comprising a dopamnine agonist dispersed in an aqueous or non-aqueous delivery vehicle. The aqueous vehicle is selected from pure water, substantially pure water or water combined with other excipients such as salts, ions or other excipients which are generally used in aqueous based systems. The liquid formulations are in the form of solution based dispersions or solutions in solvents or cosolvents such as alcohols or glycols with water. Non-aqueous solutions include those alchohol or glycol based systems which may have some water but which are not comprised of a majority percentage of water and which are known to those of skill in the art as effective and safe delivery vehicles. Non-aqueous solutions also include those systems containing halogenated hydrocarbons. Administration of liquid formulations in the form of drops or dispersions occurs through the nose and/or trachea to facilitate absorption of the formulation and pro-drug and/or active ingredients into the lungs and ultimately delivery to the dopamine receptors where the medicinal effect is achieved to treat, for example, Parkinson's disease or conditions resulting from substance abuse such as self-administration of cocaine. Devices may be utilized to assist in the delivery of the drug(s).

In another embodiment, the present invention provides a pharmaceutical composition for aerosol delivery of a dopamine agonist comprising a dopamine agonist, a propellant, poloxamer and tocopherol.

In another embodiment, the present invention provides a method of administering a dopamine agonist to a patient comprising administering to the patient a therapeutically effective amount of the aerosol composition described above.

In another embodiment, the present invention provides a method of administering a dopamine agonist to a patient comprising administering to the lungs of the patient a therapeutically effective amount of the liquid formulation described above.

DETAILED DESCRIPTION OF THE INVENTION

It is expected that numerous chlorofluorocarbon (CFC) and non-chlorofluorocarbon (NCFC) aerosol propellants may be used with the compositions and methods of the present invention. Preferred CFC propellants are CFC-11 (trifluorochloromethane), CFC-12 (dichlorodifluoromethane) and CFC-114 (dichlorotetrafluoroethane). Especially preferred propellants are non-ozone depleting halogenated alkanes such as HCFC-123 (1,1,1-trifluoro-2,2-dichloroethane), HCFC-124 (1,1,1,2-tetrafluorochloroethane), HCFC-141b, HCFC-225, HFC-125, FC-C51-12 (perfluorodimethylcyclobutane), DYMEL A (dimethyl ether) and DYMEL 152a (1,1-difluoroethane). More preferred propellants are HFC-134a and HFC-27ea; HFC-134a being most preferred.

The poloxamers utilized in the compositions of the present invention are block copolymers of ethylene oxide and propylene oxide having the following structures:

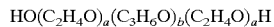

and

wherein a and b are the approximate number of repeating ethyleneoxy or propyleneoxy units. The poloxamers are included in the FDA Inactive Ingredients Guide (IV injections, inhalations, optthalmic preparations, oral powders, solutions, suspensions and syrups, and topical preparations).

The poloxamers useful in the compositions of the present invention have a molecular weight of from about 1950 to about 3350 and a hydrophilic lipophilic balance (hlb) of from about 10 to about 20. Representative poloxamers include poloxamer 124 (Pluronic® L44, MW about 2200, hlb 16), Pluronic® 10R5 (MW about 1950, hlb 15), Pluronic® 17R4 (MW about 2650, hlb 12), Pluronic® 22R4 (MW about 3350, hlb 10) and Pluronic® L64 (MW about 2900, hlb 15), all available from BASF Corp., Parsippany, N.J.

The poloxamer may be present in a concentration of from about 0.001% to about 5%, preferably in a concentration of from about 0.01% to about 2% and most preferably in a concentration of from about 0.1% to about 1%.

Preferred poloxamers have a molecular weight of from about 1950 to about 2900 and an hlb of from about 12 to about 16.

The most preferred poloxamer of the present invention is poloxamer 124.

Poloxamer 124 has the chemical name α-hydro-ωhydroxypoly(oxyethylene)poly(oxypropylene)poly(oxyethylene) block copolymer and has the formula

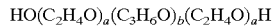

wherein a is about 12 and b is about 20. As listed in USPNF XVII poloxamer 124 has a molecular weight of between 2090 and 2360 and a hlb of 16. It is a liquid at ambient temperature and has weight percent oxyethylene of 46.7%±1.9% and unsaturation (mEq/g) of 0.020±0.008 see Wade, A. and Weller P. L., eds., *Handbook of Pharmaceutical Excipients*, (2 ed., Washington, D.C.: American Pharmaceutical Assoc.) 1994, 352–354. Pluronic® L44 has a molecular weight of about 2250.

The aerosol compositions of the present invention may also contain additonal inactive excipients such as antioxidants and flavoring and/or taste masking agents to stabilize the drug and improve dosimetry. Preferred antioxidants are tocopherol derivatives such as d-alpha tocopherol, dl-alpha tocopherol, d-alpha tocopherol acetate, dl-alpha tocopherol acetate d-alpha tocopherol acid succinate and dl-alpha tocopherol acid succinate. The most preferred antioxidant is dl-alpha tocopherol acetate. The antioxidant may be present in a concentration of from about 0.001% to about 5%, preferably in a concentration of from about 0.01% to about 2% and most preferably in a concentration of from about 0.01% to about 1%.

A sweetner such as aspartame and/or a taste masking agent such as menthol may also be present in concentrations of between about 0.001% and and about 10% by weight, preferably in a concentration of between about 0.002% and about 5% by weight and more preferably in a concentration of between about 0.01% and 1%.

The preparation and therapeutic use of representative dopamine agonists for incorporation into compositions in accordance with the present invention are disclosed in the following publications:

1. U.S. Pat. No. 5,597,832, issued
2. Brenner, et al., U.S. Pat. No. 4,340,600, issued;
3. Brenner, U.S. Pat. No. 4,282,227, issued;
4. Nichols, et al., U.S. Pat. No. 5,047,536, issued Sep. 10, 1991;
5. Nichols, et al., PCT Application WO9324462, published Dec. 9, 1993;
6. P. H. Andersen et al., *European Journal of Pharmacology*, 1987, 137, 291–292.
7. Brewster, et al., *J. Med. Chem.*, 1990, 33, 1756–1764;
8. H. E. Katerinopoulos and D. I. Schuster, "Structure-Activity Relationships for Dopamine Analogs: A Review", in *Drugs Of The Future*, 1987, 12, 223–253.

The preferred dopamine agonists of the present invention are disclosed in U.S. Pat. No. 5,597,832 which is incorporated herein by reference, and has formula I

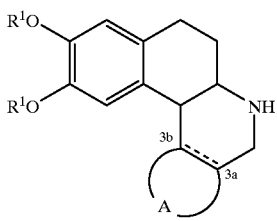

I or a pharmaceutically acceptable salt, ester or prodrug thereof wherein:

$R^1$ is hydrogen or a readily-cleavable group.

A and the atoms to which it is attached define a heterocyclic ring selected from the group consisting of

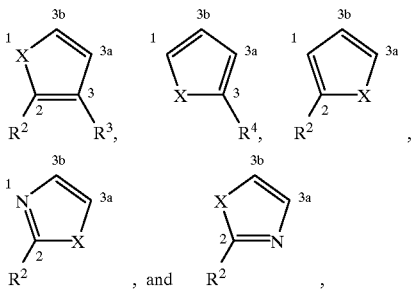

wherein X is sulfur or oxygen, $R^2$ is hydrogen, Cl, $CF_3$, $C_1$–$C_6$-alkyl, $C_3$–$C7$-cycloalkyl, —$CH_2$—$C_3$–$C_5$-cycloalkyl, phenyl or thiophene, $R^3$ is hydrogen, or when $R^2$ is hydrogen, Cl, $C_1$–$C_6$-alkyl or $CF_3$, then $R^3$ is additionally Cl, $C_1$–$C_5$-alkyl or $CF_3$, and $R^4$ is hydrogen, Cl, $C_1$–$C_6$-alkyl, or $C_3$–$C_7$-cycloalkyl.

The most preferred compound of the present invention is (5aR-trans)-4,5,6,7,11b -hexahydro-2-propylbenzo[f]thieno [2,3-c]quinoline-9,10-diol, diacetate (ester) hydrochloride (II)

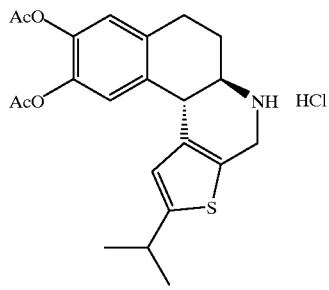

II which is a prodrug of the dopamine agonist (5aR-trans)-4, 5,6,7,11b-hexahydro-2-propylbenzo[f]thieno[2,3-c] quinoline-9,10-diol (III).

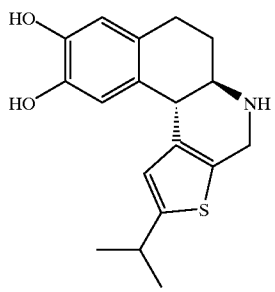

III

These compounds may be prepared by, for example, reacting a chiral starting material of formula (2)

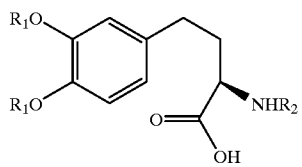

(2)

wherein $R_1$ is a catechol-protecting group and $R_2$ is an amino-protecting group at $-25°$ C. with N-methylmorpholine and isobutylchloroformate followed by reation with dihydroxylamine to give the chiral intermediate compound of formula (3)

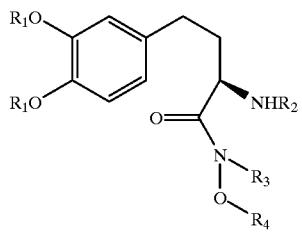

(3)

wherein $R_1$ and $R_2$ are as defined above for formula (2) and $R_3$ and $R_4$ are each methyl, or $R_3$ and $R_4$ taken together are —$CH_2$—$CH_2$—$CH_2$—, and reacting the compound of formula (3) with a nucleophilic reagent of formula (4)

(4)

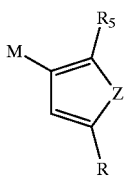

wherein R is selected from hydrogen or C1–C6alkyl and Z is oxygen, sulfur or —CH=CH— and M is an alkali metal or the Grignard (MgX) moiety, and $R_5$ is hydrogen, hydroxymethyl or a hydroxymethyl-equivalent group to form a compound of formula (5)

(5)

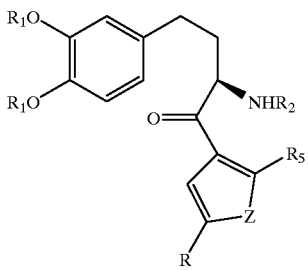

with the variables as defined above and reducing the compound of formula (5) to the chiral compound of formula (6)

(6)

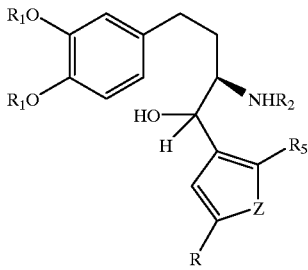

and cyclizing the compound of formula (6) in the presence of a Lewis acid and a suitable solvent to give the chiral trans compound of formula (7)

(7)

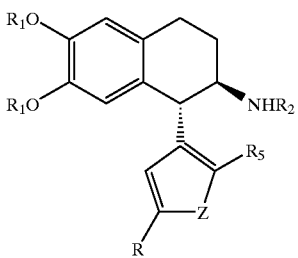

with the variables as defined above and removing the $R_2$ and optional hydroxymethyl equivalent protecting groups and cyclizing the compound of formula (7) under suitable conditions to give the chiral intermediate of formula (8)

(8)

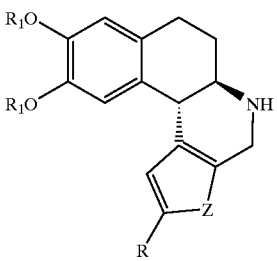

wherein R, $R_1$ and Z are as described above; and optionally removing the catechol protecting groups from the compound of formula (8) to provide a compound of the formula:

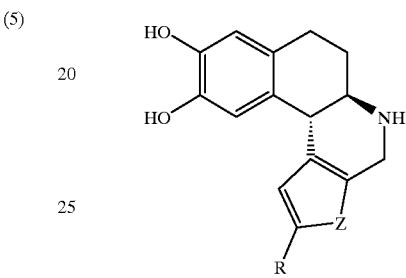

The suitable conditions to go from (7) to (8) are, for example, adding to a solution of the amine compound trans-(1S,2R)-6,7-Dimethoxy-1,2,3,4-tetrahydro-1-(2-propyl-4-thienyl)-2-napthylamine in absolute ethanol is added 37% formaldehyde in water. The reaction is stirred at room temperature for 15 minutes and then concentrated HCl is added and the reaction is heated at reflux for 4 hr. The reaction is then cooled and the suspension is diluted with ether and stirred at room temperature for 1 hr. The mixture is then filtered and dried to give, for example, a white crystalline solid of trans-(5aR, 11bS)-9,10-dimethoxy-4,5,5a,6,7,11b-hexahydro-2-propyl-3-thia-5-aza-cyclopenta[c]phenanthrene hydrochloride which can be deprotected to form the diol. This diol can be acetylated to form, for example, the compound of Example 1.

The term "$C_1$–$C_5$-" or "$C_1$–$C_6$-alkyl" as used herein means a straight- or branched-chain hydrocarbon radical containing from one-to-five or from one-to-six carbon atoms, as indicated, including as appropriate, for example, methyl, ethyl, n-propyl, i-propyl, n-butyl, sec-butyl, i-butyl, t-butyl, pentyl, hexyl, and the like.

The term "$C_3$–$C_7$-" or "$C_3$–$C_5$-cycloalkyl" as used herein means a cyclic hydrocarbon ring containing from three-to-seven carbon atoms or from three-to-five carbon atoms, including, for example, as appropriate, cyclopropyl, cyclobutyl, cyclopentyl, cyclohexyl or cycloheptyl.

The dopamine agonists useful in the compositions of the present invention include not only those specifically named above, but also where appropriate the pharmaceutically acceptable salts, esters, amides and prodrugs thereof. By "pharmaceutically acceptable salts, esters, amides and prodrugs" is meant those carboxylate salts, amino acid addition salts, esters, amides and prodrugs of a compound which are, within the scope of sound medical judgement, suitable for use in contact with with the tissues of humans and lower animals with undue toxicity, irritation, allergic response and the like, commensurate with a reasonable benefit/risk ratio and effective for their intended use. In particular, the term "salts" refers to the relatively non-toxic, inorganic and organic acid addition salts of a medicinal compound. These salts can be prepared in situ during the final isolation and purification of the compound or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berge, et al., "Pharmaceutical Salts," *J. Pharm. Sci.,* 66:1–19 (1977), incorporated herein by reference.)

Examples of pharmaceutically acceptable, non-toxic esters of a compound include ($C_1$-to-$C_6$ alkyl) esters wherein the alkyl group is a straight or branched chain. Acceptable esters also include ($C_5$-to-$C_7$ cycloalkyl) esters as well as arylalkyl esters such as, but not limited to, benzyl; ($C_1$-to-$C_4$ alkyl) esters are preferred.

The term "prodrug" refers to compounds that are rapidly transformed in vivo to yield the parent medicinal compound, as for example by hydrolysis in blood. A thorough discussion is provided in T. Higuchi and V. Stella, "Pro-drugs as Novel Delivery Systems", Vol 14 of the A.C.S. Symposium Series, and in *Bioreversible Carriers in Drug Design,* ed. Edward B. Roche, American Pharmaceutical Association and Pergamon Press (1987), both of which are incorporated herein by reference.

When used in the above compositions, a therapeutically effective amount of a medicament of the present invention may be employed in pure form or, where such forms exist, in pharmaceutically acceptable salt, ester or prodrug form. By a "therapeutically effective amount" of a medicament is meant a sufficient amount of the compound to obtain the intended therapeutic benefit, at a reasonable benefitrisk ratio applicable to any medical treatment. It will be understood, however, that the total daily usage of the medicaments and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses at levels lower than required to achieve the desired therapeutic effect and to gradually increase the dosage until the desired effect is achieved.

The term "readily-cleavable group", as used herein, means substituents which are readily cleaved in vivo, for example, by hydrolysis in blood or tissue, to yield the compound of Formula (I) wherein $R^1$ is hydrogen. Readily-cleavable groups include those substituents commonly referred to as "prodrug moieties", see, e.g., T. Higuchi and V. Stella who provide a thorough discussion of the prodrug concept in *Pro-drugs as Novel Delivery Systems,* Vol. 14 of the A.C.S. Symposium Series, American Chemical Society (1975). Examples of readily-cleavable groups include acetyl, trimethylacetyl, butanoyl, methyl succinoyl, t-butyl succinoyl, ethoxycarbonyl, methoxycarbonyl, benzoyl, 3-aminocyclohexylidenyl, and the like.

The total daily doses of the dopamine agonist contemplated for use with this invention, and consequently the concentrations by weight of the dopamine agonist in the respective compositions, may vary widely. The intended daily dose may range from about 0.01 to 50 mg/kg body weight or more, usually from 0.1 to 30 mg/kg body weight; accordingly, where an aerosol inhaler is to be used several times a day with a discharge volume of between about 5 and about 250 μL, the concentration of medicament will be between about 0.2 and about 100 mg/mL. In the case of a dopamine agonist expected to be administered in a daily dose ranging from about 0.01 to about 50 mg/kg/day, the concentration will be between about 0.001 and about 500 mg/mL. Of course, medicament concentrations outside of these ranges may also be suitable, where different potencies, dosing frequencies and discharge volumes are used.

The MDI compositions of the invention may be prepared by combining poloxamer and any other excipients with a medicament which has been milled or otherwise reduced to a desired particle size, and placing the mixture in a suitable aerosol container or vial. After sealing the container, an aerosol propellant is introduced and the system is agitated to fully blend the ingredients. In some instances, it may be necessary to wet-mill the medicament in a closed system, as for example under temperature and pressure conditions which permit the medicament to be milled while mixed with a liquid-phase aerosol propellant. It is expected that, for any particular combination of medicament, propellant and poloxamer, the ideal order of addition of ingredients and the conditions under which they are to be combined may readily be determined.

The compositions and methods of the present invention will be better understood in connection with the following examples, which are intended as an illustration of and not a limitation upon the scope of the invention.

EXAMPLE 1

Preparation of MDI Formulations for Performance Testing

For a typical lab-scale process, about 50 g (5aR-trans)-4,5,6,7,11b-hexahydro-2-propylbenzo[f]thieno[2,3-c]quinoline-9,10-diol, diacetate (ester) hydrochloride (prepared by, for example, the methods described in U.S. Pat. No. 5,597,832 incorporated herein by reference or as otherwise described herein) was weighed and added to about 480 ml glass beads in the DYNO mill. The milling chamber was then sealed, 2000 mL of HFC-134a added, and the system chilled to −10° C. at a pressure of approximately 65 psi. The contents in the milling chamber were milled for about 1 hour, after which about 1 g of vitamin E and 8 g poloxamer 124 were transferred to the slurry. After recirculating to uniformly disperse the solids in the formulation, 10 mL of the final slurry was fried into glass vials or aluminum cans previously crimped with 150 (1 valves. All formulations were subjected to evaluation of in vitro functional performance tests after 24 hours of manufacture. Large scale (i.e., 12–15 L) batches were also prepared in a similar fashion.

EXAMPLE 2

Dispersion Quality of MDI Formulations

A determination of the dispersion quality of several MDI formulations prepared with HFA-134a was conducted as follows: Pluronic® L44 (BASF Corp., Parsippany, N.J.), drug and excipients being formulated were combined in the amounts shown in appropriate transparent aerosol containers (vials). The vials were crimped using a 100 µL Valois metered valve and charged with approximately 10 mL of HFC-134a. The container was shaken for about 30 minutes to blend the ingredients. The dispersion quality in each preparation was evaluated visually after 24 hours using the following criteria:

Poor: Phase separation; top phase clear, bottom phase containing solids

Fair: Partial phase separation; cloudiness in the top phase

Good: Grainy appearance; no phase separation

Excellent: Milky homogeneous appearance; no phase separation

Results of these tests are shown below in Table 1. The data obtained show that the formulations of the present invention maintain a high degree of dispersion even after 24 hours.

TABLE 1

Dispersion Quality of (5aR-trans)4,5,6,7,11b-hexahydro-2-propylbenzo[f]thieno[2,3-c]quinoline-9,10-diol, diacetate(ester)hydrochloride in HFC-134a

| mg Drug | Pluronic ® L44 | mg Tocopherol acetate | Suspension Quality |
|---|---|---|---|
| 20 | 0 | 0 | good |
| 40 | 0 | 0 | good |
| 20 | 3 | 0 | good |
| 40 | 3 | 0 | good |
| 20 | 5 | 0 | good |
| 40 | 5 | 0 | good |
| 20 | 3 | 2 | good |
| 40 | 3 | 2 | good |
| 20 | 5 | 2 | good |
| 40 | 5 | 2 | good |

EXAMPLE 3

Uniformity of MDI Delivery

Delivery uniformity of the MDI compositions of the present invention was tested as follows: An aersol having the following composition 5aR-tans)-4,5,6,7,11b-hexahydro-2-propylbenzo[f]thieno[2,3-c]quinoline-9,10-diol, diacetate (ester) hydrochloride (250 mg), d-α tocopherol acetate (5 mg), Pluronic® L44 (40 mg) and HFC-134a (10 mL, 12.2 g) was prepared as described above. Each container was shaken and it valve primed by aerosolizing 5 times in succession. After priming, the aerosol container was shaken and then attached to an atomizing nozzle which was cut from an actuator. With the nozzle pointed downward, the canister was placed into a 30-mL beaker containing 10 mL of methanol until the nozzle touched the bottom of the beaker. Then, a total of 2 sprays, each separated by a 5 second pause, was delivered into the beaker. The valve stem and ferrule were rinsed with acetonitrile. The amount of drug in each sample was analyzed by HPLC.

TABLE 2

| | Shot Weight (mg/2 sprays) | |
|---|---|---|
| Spray # | Can 1 | Can 2 |
| 3, 4 | 375.9 | 375.05 |
| 13, 14 | 373.5 | 365.8 |
| 23, 24 | 365.1 | 369.0 |
| 33, 34 | 382.8 | 363.4 |
| 43, 44 | 374.8 | 378.8 |
| 53, 54 | 372.3 | 371.5 |
| 59, 60 | 370.3 | 364.8 |
| 63, 64 | 336.4 | 224.6 |
| 65, 66 | 157.2 | 193.4 |

The shot weight data, shown below in Table 2, demonstrate the uniformity with which the MDI compositions of the present invention are delivered.

EXAMPLE 4

Effect of Actuator Orfice Diameter on Ex-Actuator Dose Deliver

A proposed USP Dosage Unit Sampling Apparatus was used for all samples investigated in the study. Parts of the apparatus, including vacuum connector, filter membrane, sample collection tube and mouthpiece adapter, were assembled and the valve of the aerosol container was activated at the beginning of its first use by spraying 2 times to waste as follows: the aerosol container was shaken gently for 10 seconds (about 8 times) and then attached to an atomizing nozzle connected to the actuator, the inhaler was discharged to waste for approximately 1 second using thumb and forefinger, then, the canister was gently shaken for another 10 seconds and discharged again to waste. The canister was then accurately weighed and its weight recorded.

After the second priming spray, each container was gently shaken and discharged into the sampling apparatus through the mouthpiece adapter, with the vacuum pump running at 30±1.5 L/min. One minute later, the second shot was delivered to the apparatus again after shaking for 10 seconds. The process was repeated until a total of 3 sprays were delivered. Sixty seconds after the second spray, the inhaler was detached from the Dosage Unit Sampling Apparatus, and disconnected from the vacuum. The canister was weighed again and its weight was recorded. The filter and interior of the apparatus were rinsed with the sampling solvent (50% acetonitrile in water) and diluted to a final volume of 50 mL.

For each aerosol can tested, a total of 3 doses were collected and analyzed, i.e., dose 1 (spray 3–5), dose 2 (spray 30–32), dose 3 (spray 58–60). For determination of the drug remaining in the actuator, the actuator was rinsed with the sampling solution and diluted to a final volume of 25 mL. The drug content in the final sample solution was analyzed using HPLC. The results, expressed as mg's of (5aR-trans)-4,5,6,7,11b-hexahydro-2-propylbenzo[f]thieno[2,3-c]quinoline-9,10-diol (III), are summarized in Table 3.

TABLE 3

Effect of Actuator Orfice Diameter on Ex-Actuator Dose Delivery

|  | | III (mg/3 sprays) | | | |
|---|---|---|---|---|---|
|  | Cans | Sprays 3–5 | Sprays 30–32 | Sprays 58–60 | Grand mean |
| Actuator Orifice 0.4 mm | 4 | 3.31 ± 0.30 | 2.98 ± 0.21 | 3.09 ± 0.35 | 3.13 ± 0.30 |
| Acturator Retention Ex-actuator Dose | 4 | 4.52 ± 0.34 | 4.70 ± 0.36 | 4.47 ± 0.54 | 4.56 ± 0.40 |
| % Actuator Retention | | | 40.7 | | |
| Actuator Orifice 0.5 mm | 4 | 4.22 ± 1.00 | 3.70 ± 0.35 | 3.74 ± 0.49 | 3.88 ± 0.66 |
| Acturator Retention Ex-actuator Dose | 4 | 3.91 ± 0.20 | 3.11 ± 0.57 | 3.68 ± 0.81 | 3.57 ± 0.64 |
| % Actuator Retention | | | 52.1 | | |

In the case of orifice diameter 0.5 mm, a higher percentage of dose (about 52%) was lost in actuator compared the orifice diameter 0.4 mm even though the through-can dose uniformity was satisfactory. These data suggest that the actuator with orifice diameter 0.4 mm could deliver higher ex-actuator dose in comparison of the actuator with 0.5 mm of orifice diameter.

EXAMPLE 5

Aerosol Particle Size Distribution

Particle size data of the above compound in an aerosol formulation were determined using the Malvern laser diffraction particle sizer (Model 2600C). Samples were analyzed as aerosolized aprays in air. The aerosol can with an actuator assembly was mounted on a clamp stand so that the spray jet was 12.5 cm from the laser beam. Beam length, i.e., the length of aerosol flume along the path of the laser bean, was about 10 cm. In this configuration, the distance of the objective lens was 3 cm from the middle of the aerosol flume, and the IR beam of the spray synthronizer was 4 cm from the spray jet. Also, the laser beam and the IR beam were parallel and approximately 8.5 cm apart. A total of 10 sprays were actuated and analyzed individually assuming a log-normal distribution model. The detection of spray duration was approximately 15 milliseconds (ms), i.e., beginning from 70 ms and ending at 85 ms after interruption of the IR beam by the aerosol.

The particle size of aerosolized product determines the extent as well as the pattern of drug deposition in the respiratory tract. A summary of particle size distribution data in a prototype formulation of the above compound aerosol formulation is provided in Table 4 presented below. In general, about 40% of the particles emitted from the valve and the actuator system had a value of $\leq 4.7$ $\mu$m in diameter with about 90% of the emitted particles being less than 10 $\mu$m. The present invention is therefore directed to a method of delivering a dopamine agonist having an emitted particle size of less than 10 $\mu$m to a patient in need of treatment thereof and in particular relates to a method of delivering a dopamine agonist selected from those described in, for example, U.S. Pat. No. 5,597,832, to a patient in need of treatment thereof for the treatment of substance abuse or Parkinson's disease. The present invention is also directed to formulations containing such a drug in combination with propellants and excipients as described herein wherein the emitted particle size of the drug or dopamine agonist, such as those described in U.S. Pat. No. 5,597,832 or more particularly to the compound identified above, has the values of less than 10 $\mu$m in diameter and preferrably less than or equal to about 5.0 $\mu$m in diameter.

TABLE 4

Particle Size Distribution of the Aerosol Formulation of Example 1

| size range ($\mu$m) | % of particle volume in the size range (Lot 1) | % of particle volume in the size range (Lot 2) |
|---|---|---|
| 8.2–6.4 | 10.2 | 13.0 |
| 6.4–5.0 | 16.6 | 18.7 |
| 5.0–3.9 | 20.5 | 20.6 |
| 3.9–3.0 | 19.3 | 17.1 |
| 3.0–2.4 | 13.8 | 11.1 |
| 2.4–1.9 | 7.6 | 5.6 |
| 1.9–1.5 | 3.3 | 2.3 |
| 1.5–1.2 | 1.2 | 0.8 |
| Mean($\mu$m) | 5.9 | 4.5 |
| % <47 $\mu$m | 41.4 | 53.2 |
| 90% less than ($\mu$m) | 9.6 | 8.3 |

EXAMPLE 6

Bioavailability of MDI Compositions

The bioavailability of the formulations were assessed in a non-crossover bioavailability study using 5 mgs of the compound of Example 1 in the suspension aerosol formulation and an iv injection solution. The aerosol sprays were delivered anteriorly via a tracheal stoma in each subject animal (beagle dog). Plasma concentration profiles of the active metabolite of the compound of example 1 (e.g. the diol) following administration of the formulations are summarized in Table 5 below. The values of Cmax for two lots of the product were 11.4 (±2.7) ng/mL and 13.3 (±9) ng/mL, respectively, and the estimates of $AUC_{0-24}$ were 26.9 (±3.4) ng/mL and 33.2 (±10.6) h×ng/mL, respectively. The lung bioavailability of the compound of Example 1 with the HFC formulation was higher than 27% compared to the intravenous injection. These results demonstrate that lung absorption of the compound of Example 1 following inhalation delivery to the animals occurs more efficiently than I.V. administration. In addition, Table 5 shows that the rate of absorption of the compound of Example 1 is fast with a Tmax of less than 20 min. This shows that the compound of Example 1 suspended in, for example, HFC-134a is well absorbed upon delivery to the lungs.

TABLE 5

Pharmacokinetic Summary Following Intravenous and Inhalation Delivery of the Compound of Example 1 to Dogs[a]

| Route | Lot No. | n | Tmax (h) | Cmax (ng/mL) | $AUC_{0-24}$ (h ng mL$^{-1}$) | F (%) |
|---|---|---|---|---|---|---|
| Intravenous | | 6 | N/A | | 19.3 ± 7.4 | 100.00 |
| Inhalation | 1 | 4 | 0.2 ± 0.1 | 11.4 ± 2.7 | 26.9 ± 3.4 | 27.9 ± 3.5 |
| | 2 | 4 | 0.1 ± 0.1 | 13.3 ± 0.9 | 33.2 ± 10.6 | 34.3 ± 11.0 |

[a] 5 mg of the compound of Example 1 was dosed to 4 dogs by inhalation or 0.1 mg eq/kg by intravenous injection of a non-aerosol formulation (liquid formulation containing the compound of example 1).

EXAMPLE 7

Non-aerosol Liquid Formulation(s)

A liquid formulation which is administered to a patient in need of treatment thereof comprises a dopamine agonist dispersed in an aqueous or non-aqueous system. The aqueous system may be pure or substantially pure water or may have pharmaceutically acceptable liquid excipients or diluents which assist in or are effective in assisting the delivery or performance of the compound of example 1 into the airways by non-propellant based means. The preferred excipient added to an aqueous based delivery system was selected from mannitol. The liquid composition administered intratracheally comprises the compound of example 1 (6.9 mgs/vial); water and mannitol (U.S. Pat. No. 4,4403, 100.0). Cosolvents may be added to aid in the solubility of aqueous insoluble dopamine agonists. These cosolvents are selected from pharmaceutically acceptable alcohol or glycol based organic solvents.

A liquid formulation containing the compound of Example 1 was administered intratracehally to tracheaotomized dogs wherein the dogs had a hole in the trachea for administration of the liquid formulation through a flexible tube. The viscosity of the administered solution was similar to water and the dose was squirted into the tube via pressure from a syringe filled with the liquid formulation. This formlation would not be administered through nasal or mouth means.

The solution used in the intratracheal administration contained the following:

Mannitol, USP 10 mg/ml

Compound of example 1 6.9 mg/ml (diol Equiv.) 5.0 mg/ml with water for Injection as the solvent.

0.1 mg/kg (approximately 0.5 ml each) was administered to the dogs and the drug was effectively delivered. The above percentages may be varied by one of ordinary skill in the art to provide various dosages and/or ratios of the above excipients or compounds.

The above examples demonstrate that an aerosol formulation as recited above comprising a dopamine agonist is effectively delivered through the lungs to provide sufficient bioavailability of a dopamine agonist such as the compound of example 1 in the form of its diester, monoester or catechol using poloxamers (such as 124) and vitamin E in tetrafluroethane (HFC-134a). The compounds were delivered using 150 μL metering valves wherein each actuation of the valve delivered approximately 2.73 mg equivalents of the diol form of example 1. When corrected for device losses, this amounted to delivery of approximately 1.65 mg equivalents of the diol. The formulations contained 25 mg/mL of the compound of Example 1 which is equivalent to 18.1 mg/mL of the diol compound. Each canister contained 10 mL of aerosol product and a total of 60 sprays could be 5 reproducibly delivered in terms of drug content. The average ex-actuator delivery of diol equivalents of the compound of Example 1 was 4.56±0.40 mg/3 sprays when an actuator with 0.4 mm orifice diameter was utilized. The actuator retention of the drug was approximately 40%. When the actuator orifice diameter was increased to 0.5, the mean ex-actuator delivery was decreased to 3.57±0.64 mg 3 sprays and the actuator retention was increased to 52.1%. The preferred method of delivery therefore utlizes orifice diameters which delivery sufficient quantity of drug to be effective.

The examples also show that delivery using the aerosol formulation is as effective or more effective than delivering the drugs through i.v. injection which was utilized as a control. In addition, the drugs were administered intratracheally which resulted in effective delivery of liquid formulations containing or comprising a dopamine agonist.

The present invention therefore relates to a method of delivering dopamine agonists through the airways of a mammal or human comprising adminstering a solid, liquid or aerosol dopamnine agonist formulation to said mammal or human. More particularly, the invention relates to pulmonary delivery of a dopamine agonist selected from the generic or specific compounds described herein. The dopamine agonist formulations are designed for the specific route of delivery with aerosol means used for propellant based formulations and with liquid or solid means used for, for example, intratracheal administration. The present invention includes any form of pulmonary delivery of a dopamine agonist to a patient.

What is claimed is:

1. A method of administering a dopamine agonist to a patient in need of such treatment comprising administering to the patient a therapeutically effective amount of a pharmaceutical composition comprising a dopamine agonist, a propellant and poloxamer.

2. A method according to claim 1 wherein the propellant is selected from the group consisting of CFC-11, CFC-12, CFC-114, HCFC 123, HCFC 124, HCFC 141b, HCFC 225, HCFC 125, perfluorodimethylcyclobutane, dimethyl ether, 1,1-difluoroethane, HFC 134a and HFC 227ea.

3. A method according to claim 2 wherein the propellant is selected from the group consisting of HCFC 123, HCFC 124, HCFC 141b, HCFC 225, HCFC 125, perfluorodimethylcyclobutane, dimethyl-ether,1,1-difluorethane, HFC 134a and HFC 227ea.

4. A method according to claim 3 wherein the dopamine agonist is present in a concentration of from about 0.001% to about 15% by weight, the poloxamer is present in a concentration of from about 0.001% to about 5% by weight, and tocopherol is present in a concentration of from about 0.001% to about 5% by weight.

5. A method according to claim 3 wherein the poloxamer is selected from block copolymers of ethylene oxide and propylene oxide having a molecular weight of between about 1950 and 3350 and a hydrophilic lipophilic balance of between about 10 and about 20.

6. A method according to claim 3 wherein the tocopherol is selected from the group consisting of d-alpha tocopherol, dl-alpha tocopherol, d-alpha tocopherol acetate, dl-alpha tocopherol acetate d-alpha tocopherol acid succinate and dl-alpha tocopherol acid succinate.

7. A method according to claim 3 wherein the dopamine agonist is a compound of formula

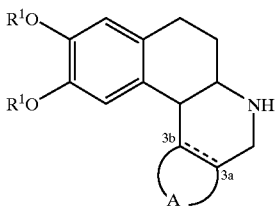

or a pharmaceutically acceptable salt, ester or prodrug thereof wherein:

R¹ is hydrogen or a readily-cleavable group;

A and the atoms to which it is attached define a heterocyclic ring selected from the group consisting of

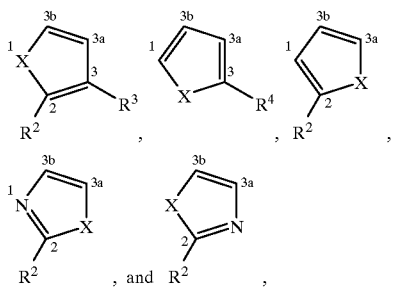

wherein

X is sulfur or oxygen, $R^2$ is hydrogen, Cl, $CF_3$, $C_1$–$C_6$-alkyl, $C_3$–$C_7$-cycloalkyl, —$CH_2$—$C_3$–$C_5$-cycloalkyl, phenyl or thiophene, $R^3$ is hydrogen, or when $R^2$ is hydrogen, Cl, $C_1$–$C_6$-alkyl or $CF_3$, then $R^3$ is additionally Cl, $C_1$–$C_5$-alkyl or $CF_3$, and $R^4$ is hydrogen, Cl, $C_1$–$C_6$-alkyl, or $C_3$–$C_7$-cycloalkyl.

8. A method according to claim 7 wherein the propellant is selected from HFC-134a and HFC-227ea.

9. A method according to claim 8 wherein the dopamine agonist is present in a concentration of from about 1% to about 10% by weight, the poloxamer is present in a concentration of from about 0.01% to about 2% by weight, and tocopherol is present in a concentration of from about 0.01% to about 2% by weight.

10. A method according to claim 9 wherein the poloxamer is selected from block copolymers of ethylene oxide and propylene oxide having a molecular weight of between about 1950 and 2900 and a hydrophilic lipophilic balance of between about 12 and about 16.

11. A method according to claim 10 wherein the tocopherol is selected from d-alpha tocopherol acetate and dl-alpha tocopherol acetate.

12. A method according to claim 11 wherein the dopamine agonist is (5aR-trans)-4,5,6,7,11 b-hexahydro-2-propylbenzo[f]thieno[2,3-c]quinoline-9,10-diol, diacetate (ester) hydrochloride.

13. A method according to claim 12 wherein the poloxamer is poloxamer 124.

14. A method according to claim 12 wherein the dopamine agonist is present in a concentration of from about 1% to about 5% by weight, the poloxamer is present in a concentration of from about 0.1% to about 1% by weight, and tocopherol is present in a concentration of from about 0.01% to about 1% by weight.

15. A pharmaceutical composition for aerosol delivery of a dopamine agonist comprising a dopamine agonist, a propellant and poloxame.

16. A composition according to claim 15 wherein the propellant is selected from the group consisting of HCFC-11, CFC-12, CFC-114, HCFC 1235, HCFC 124, HCFC 141b, HCFC 225, HCFC 125, perfluorodimethylcyclobutane, DYMEL A, DYMEL 152a, HFC 134a and HFC 227ea.

17. A composition according to claim 15 wherein the propellant is selected from the group consisting of HCFC 123, HCFC 124, HCFC 141b, HCFC 225, HCFC 125, perfluorodimethylcyclobutane, DYMEL A, DYMEL 152a, HFC 134a and HFC 227ea.

18. A composition according to claim 17 wherein the dopamine agonist is present in a concentration of from about 0.001% to about 15% by weight, the poloxamer is present in a concentration of from about 0.001% to about 5% by weight, and tocopherol is present in a concentration of from about 0.001% to about 5% by weight.

19. A composition according to claim 17 wherein the poloxamer is selected from block copolymers of ethylene oxide and propylene oxide having a molecular weight of between about 1950 and 3350 and a hydrophilic lipophilic balance of between about 10 and about 20.

20. A composition according to claim 17 wherein the tocopherol is selected from the group consisting of d-alpha tocopherol, dl-alpha tocopherol, d-alpha tocopherol acetate, dl-alpha tocopherol acetate d-alpha tocopherol acid succinate and dl-alpha tocopherol acid succinate.

21. A composition according to claim 17 wherein the dopamine agonist is a compound of formula

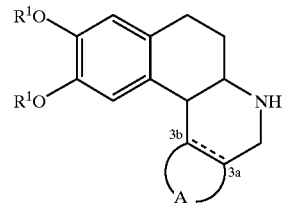

or a pharmaceutically acceptable salt, ester or prodrug thereof wherein:

R¹ is hydrogen or a readily-cleavable group;

A and the atoms to which it is attached define a heterocyclic ring selected from the group consisting of

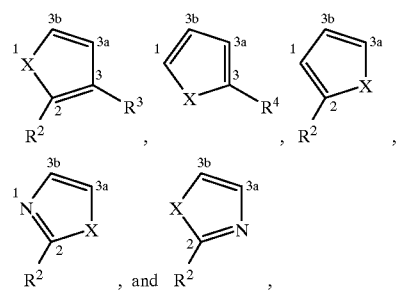

wherein

X is sulfur or oxygen, $R^2$ is hydrogen, Cl, $CF_3$, $C_1$–$C_6$-alkyl, $C_3$–$C_7$-cycloalkyl, —$CH_2$—$C_3$–$C_5$-cycloalkyl, phenyl or thiophene, $R^3$ is hydrogen, or when $R^2$ is hydrogen, Cl, $C_1$–$C_6$-alkyl or $CF_3$, then $R^3$ is additionally Cl, $C_1$–$C_5$-alkyl or $CF_3$, and $R^4$ is hydrogen, Cl, $C_1$–$C_6$-alkyl, or $C_3$–$C_7$-cycloalkyl.

22. A composition according to claim 21 wherein the propellant is selected from HFC-134a and HFC-227ea.

23. A composition according to claim 22 wherein the dopamine agonist is present in a concentration of from about 1% to about 10% by weight, the poloxamer is present in a concentration of from about 0.01% to about 2% by weight, and tocopherol is present in a concentration of from about 0.01% to about 2% by weight.

24. A composition according to claim 23 wherein the poloxamer is selected from block copolymers of ethylene oxide and propylene oxide having a molecular weight of between about 1950 and 2900 and a hydrophilic lipophilic balance of between about 12 and about 16.

25. An emitted particle composition comprising a composition according to claim 21 wherein upon delivery through an aerosol delivery device at least fifty percent of the emitted particles have an average particle size of less than or equal to 10 μm in diameter.

26. A composition according to claim 25 wherein at least 40% of the emitted particles are less than or equal to about 5.0 $\mu$m in diameter.

27. A composition according to claim 24 wherein the tocopherol is selected from d-alpha tocopherol acetate and dl-alpha tocopherol acetate.

28. A composition according to claim 27 wherein the dopamine agonist is (5aR-trans)-4,5,6,7,11 b-hexahydro-2-propylbenzo[f]thieno[2,3-c]quinoline-9, 10-diol, diacetate (ester) hydrochloride.

29. A composition according to claim 28 wherein the poloxamer is poloxamer 124.

30. A composition according to claim 29 wherein the dopamine agonist is present in a concentration of from about 1% to about 5% by weight, the poloxamer is present in a concentration of from about 0.1% to about 1% by weight, and tocopherol is present in a concentration of from about 0.01% to about 1% by weight.

31. A method of administering a dopamine agonist to a patient in need of such treatment comprising administering to the patient a therapeutically effective amount of a pharmaceutical composition comprising a dopamine agonist in the form of a fine powder or particulate.

* * * * *

UNITED STATES PATENT AND TRADEMARK OFFICE
CERTIFICATE OF CORRECTION

PATENT NO. : 6,193,954 B1
DATED : February 27, 2001
INVENTOR(S) : Akwete L. Adjei et al.

It is certified that error appears in the above-identified patent and that said Letters Patent is hereby corrected as shown below:

Column 16,
Lines 48 & 49, replace "dimethyl-ether,1,1-difluorethane," with -- dimethylether, 1, 1-difluoroethane --.

Column 17,
Line 54, replace "-4,5,6,7,11,b-" with -- 4,5,6,7,11b- --.

Column 18,
Line 2, replace "consisting of HCFC-11" with -- consisting of CFC-11 --.
Line 3, replace "HCFC 1235" with -- HCFC 123 --.

Signed and Sealed this

Seventh Day of May, 2002

Attest:

JAMES E. ROGAN
Attesting Officer     Director of the United States Patent and Trademark Office